(12) United States Patent
Lauterbach et al.

(10) Patent No.: US 9,169,167 B2
(45) Date of Patent: Oct. 27, 2015

(54) SELF-HEALING CATALYSTS: CO3O4 NANORODS FOR FISCHER-TROPSCH SYNTHESIS

(71) Applicants: Jochen A. Lauterbach, Columbia, SC (US); Jason R. Hattrick-Simpers, Irmo, SC (US); Cun Wen, Columbia, SC (US)

(72) Inventors: Jochen A. Lauterbach, Columbia, SC (US); Jason R. Hattrick-Simpers, Irmo, SC (US); Cun Wen, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/252,169

(22) Filed: Apr. 14, 2014

(65) Prior Publication Data

US 2014/0309316 A1  Oct. 16, 2014

Related U.S. Application Data

(60) Provisional application No. 61/811,390, filed on Apr. 12, 2013.

(51) Int. Cl.
  *C07C 1/04* (2006.01)
  *B01J 21/00* (2006.01)
  *C10G 2/00* (2006.01)

(52) U.S. Cl.
  CPC .............. *C07C 1/045* (2013.01); *B01J 21/00* (2013.01); *C10G 2/332* (2013.01)

(58) Field of Classification Search
  CPC ........................................................ C07C 1/045
  USPC ............................................................ 518/709
  See application file for complete search history.

(56) References Cited

PUBLICATIONS

Kang et al., Journal of Nanoscience and Nanotechnology, (2010), vol. 10, pp. 3700-3704.*
Tavasoli et al. Fuel processing technology, (2008), vol. 89, pp. 491-498.*
Santos et al. Colloids and Surfaces a Physicochem Eng Aspects (2012), 359, pp. 217-224.*

* cited by examiner

*Primary Examiner* — Yong Chu
(74) *Attorney, Agent, or Firm* — Dority & Manning, P.A.

(57) ABSTRACT

A self-healing reaction process for a chemical reaction is provided by exposing a catalyst a reaction mixture that includes carbon monoxide and hydrogen gas such that hydrocarbons are produced. The catalyst includes $Co_3O_4$ nanorods having both $Co^{2+}$ and $Co^{3+}$ exposed thereon. The $Co_3O_4$ nanorods can have a spinel crystal structure such that the $Co_3O_4$ nanorods define a $\{110\}$ facet having both $Co^{2+}$ and $Co^{3+}$ exposed thereon. During reaction conditions, water can oxidize portions of the catalyst, while the exposed $Co^{3+}$ can reduce any oxidized portions of the catalyst such that the catalyst is self-healing during reaction conditions, especially when the reaction mixture further comprises water.

7 Claims, 9 Drawing Sheets

*Fig. 5b*

SELF-HEALING CATALYSTS: CO3O4 NANORODS FOR FISCHER-TROPSCH SYNTHESIS

PRIORITY INFORMATION

The present application claims priority to U.S. Provisional Patent Application Ser. No. 61/811,390 titled "Self-Healing Catalysts: CO$_3$O$_4$ Nanorods for Fischer-Tropsch Synthesis" of Lauterbach, et al. filed on Apr. 12, 2013, the disclosure of which is incorporated by reference herein.

BACKGROUND

Heterogeneous catalysts empower more than 90% of all chemical plants worldwide and play a key role in reducing environmental pollution. Common to all catalytic processes is catalyst deactivation and the associated loss of catalytic activity, which results in a decrease in production efficiency and increased maintenance costs. Catalyst deactivation is typically addressed by altering the composition and particle size of the catalysts. Although this will lengthen catalyst lifetimes, most catalysts still require periodic time off-stream for regeneration. One of the main deactivation mechanisms is the change of the catalyst oxidation state by oxidation or reduction (redox). However, if the catalyst could be tuned to favor the reduction under reaction conditions, the catalyst could actively reduce the oxide as it grew, alleviating the need for regeneration.

Recent studies have demonstrated that tuning of the crystallographic facets exposed at the catalyst surface significantly alters the nature of surface redox reactions. For example, during electro-oxidation of formic acid and ethanol, Pt nanocrystals with high-index {730} surface facets, which contain low coordination number atoms, are more active than low-index, {111} faceted Pt nanospheres. Similarly, water oxidation is more readily catalyzed by the (040) surface of BiVO$_4$ than by (110) surfaces. Unfortunately, during such oxidative processes non-noble metal catalysts are often oxidized and deactivated. Although redox reactions can be tuned by catalyst faceting, the potential to drive in-operando healing by choosing appropriate catalyst surface orientations has not been explored.

A self-healing catalyst in oxidative environments would require the redox reaction on the catalyst surface be tuned to favor reduction of the oxide to the metallic state. Moreover, to take advantage of this functionality in heterogeneous catalysis, the redox reaction should be a side reaction rather than the primary one. For instance, in Fischer-Tropsch synthesis (FTS), the primary reaction involves the hydrogenation of CO and polymerization of hydrocarbons, with water produced as a side-product. Metallic Co is a superior FTS catalyst, but the presence of water, which reaches up to 40 vol % in industrial reactors, drives oxidative poisoning of the metallic Co. The oxidized Co is usually removed from the reaction stream and regenerated by hydrogen reduction. Thus, tuning the redox reaction to favor reduction of the oxide in-operando, would preserve the metallic Co under reaction conditions and constitute a key advance in the field of FTS.

SUMMARY

Objects and advantages of the invention will be set forth in part in the following description, or may be obvious from the description, or may be learned through practice of the invention.

A self-healing reaction process is generally provided for a chemical reaction. In one embodiment, a catalyst is exposed to a reaction mixture that includes carbon monoxide and hydrogen gas such that hydrocarbons are produced. The catalyst includes Co$_3$O$_4$ nanorods comprising both Co$^{2+}$ and Co$^{3+}$ exposed thereon. For instance, the Co$_3$O$_4$ nanorods can have a spinel crystal structure such that the Co$_3$O$_4$ nanorods define a {110} facet having both Co$^{2+}$ and Co$^{3+}$ exposed thereon.

During reaction conditions, water can oxidize portions of the catalyst, while the exposed Co$^{3+}$ can reduce any oxidized portions of the catalyst such that the catalyst is self-healing during reaction conditions, especially when the reaction mixture further comprises water.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 2c shows the reaction results for nanorods under the same conditions as FIG. 2a.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 999 nm). For example, particles having an average diameter on the nanometer scale (e.g., from about 1 nm to about 999 nm) are referred to as "nanoparticles". Particles having an average diameter of greater than 1,000 nm (i.e., 1 μm) are generally referred to as "microparticles", since the micrometer scale generally involves those materials having an average size of greater than 1 μm.

Cobalt oxide nanorods exhibit {110} facets with both $Co^{2+}$ and $Co^{3+}$ exposed on the surface, while the nanoparticles possess {111} and {001} facets, where the only surface species is $Co^{2+}$. This effect suggests that by carefully selecting the crystallographic planes of $Co_3O_4$ exposed at the catalyst surface, the reduction of the catalyst could be promoted, effectively negating oxidation during FTS.

Here, a self-healing catalyst is generally provided that is obtained by controlling catalyst crystal faceting using Co nanoparticles and nanorods as proof-of-principle. The origin of the resistance to water oxidation during FTS is illustrated via in-situ Raman spectroscopy, which shows that oxide formation on the Co nanorods surface is reversed under reaction conditions.

The self-healing functionality for the catalyst can be accomplished by tuning the crystallographic facets exposed on the active catalyst surface to promote the reduction of oxidized species. Without wishing to be bound by any particular theory, it is believed that the self-healing functionality results from the exposure of {110} surfaces on the nanorods, which present the readily reducible $Co^{3+}$ on the surface and actively reduce any water oxidized catalyst.

This concept of self-healing catalyst represents an avenue towards extending catalyst lifetimes in many catalytic reactions, such as $CO_2$ mitigation and biomass upgrading, during which water can oxidize and deactivate the catalyst. Outside the field of catalysis this approach of creating surfaces that actively reduce themselves even in oxidative environments has exciting applications, for example in creating corrosion resistant coatings. For instance, coatings could be designed for pipelines used downstream of co-fired biomass waste-derived syngas coal power boilers, which are exposed to moisture resulting in the rapid oxidation and failure of the lines.

EXAMPLES

Figure 4A:
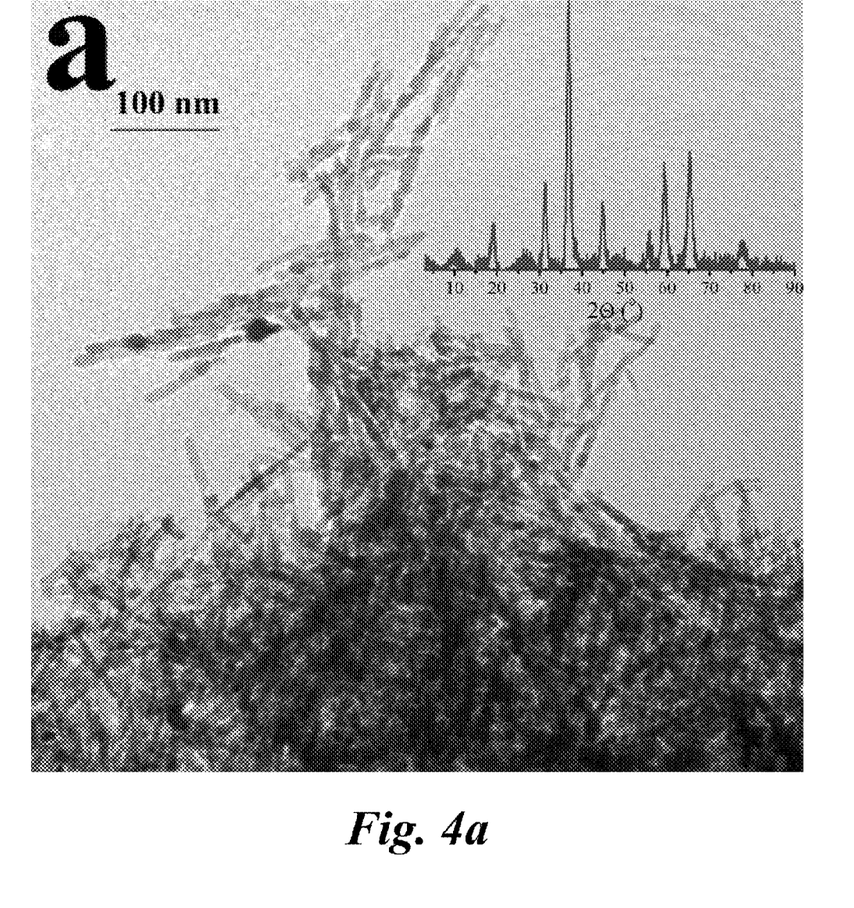
FIGS. 4a and 4b show TEM images of Co nanorods and nanoparticles, resepectively. The insets in 4a and 4b are the corresponding XRD patterns of nanorods and nanoparticles, respectively.
Figure 4B:
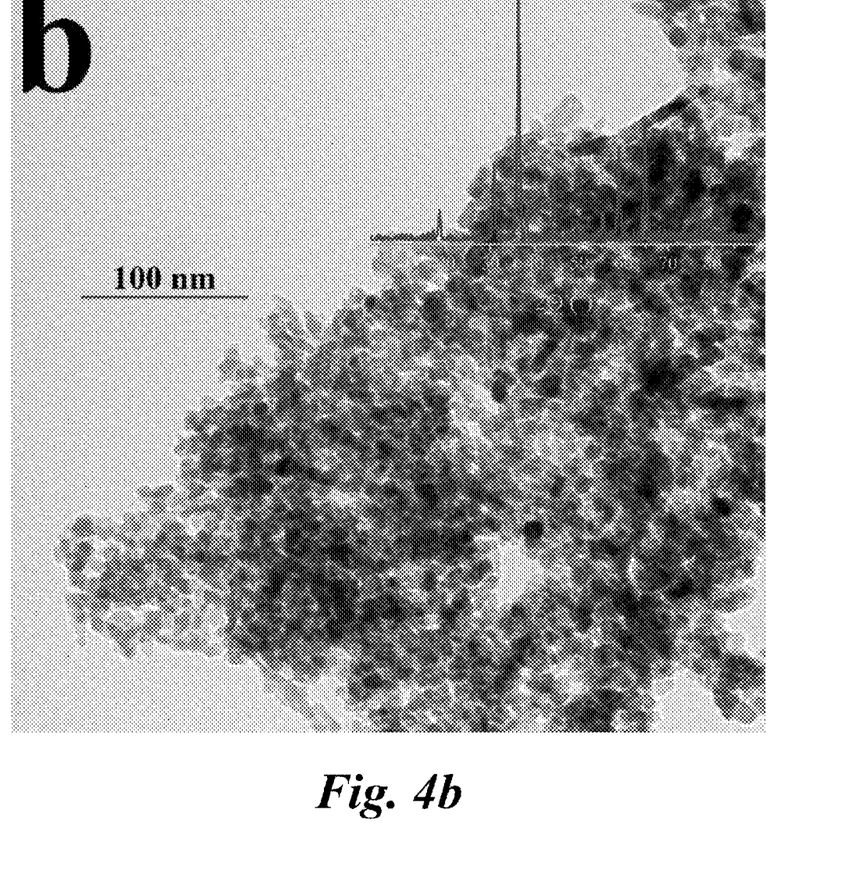

The Co nanorods and nanoparticles studied were synthesized following literature reports, and the general morphologies are shown in the transmission electron microscope (TEM) images, FIGS. 4a and 4b. The diameter of the Co nanorods was in the range of 10-20 nm, and their length was typically within 200-300 nm, which is consistent with literature. The synthesized Co nanoparticles exhibited particle sizes between 10 nm and 40 nm. The particle sizes of the nanorods and nanoparticles were comparable to the size range (10-210 nm) typically investigated for model FTS catalyst. In this range, the catalytic activity (turnover frequency) of the Co catalyst did not change with particle size; however, catalysts with particle sizes below 6 nm showed both lower activity and $C_{5+}$ selectivity. Both the as-synthesized Co nanorods and the nanoparticles have the $Co_3O_4$ spinel structure, as determined by Raman spectroscopy, powder X-ray diffraction, and nano-beam electron diffraction, see insets in FIGS. 4a and 4b. The diffraction peak located at 31.35° in the powder XRD corresponds to the (220) planes with a d-spacing of 2.85±0.06 Å (PDF 42-1467) with space group of Fd-3m.

Figure 1A:
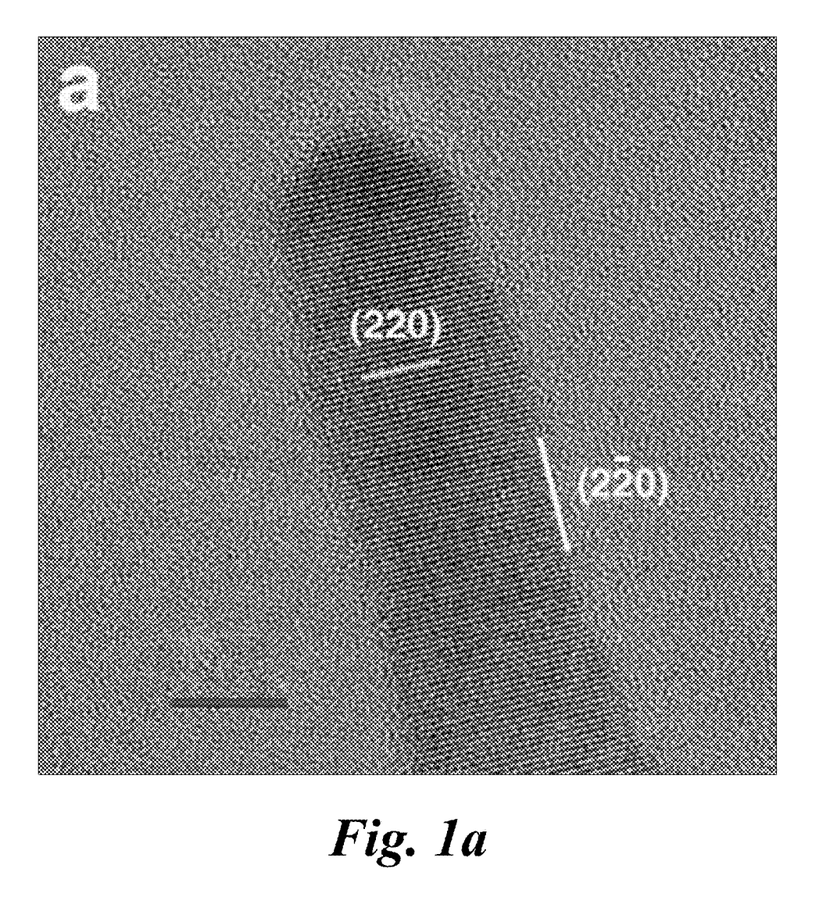
FIGS. 1a and 1b show HRTEM images of nanorods and nanoparticles, respectively, fabricated according to the Examples. The scale bar (lower right) corresponds to 5 nm.
Figure 1B:
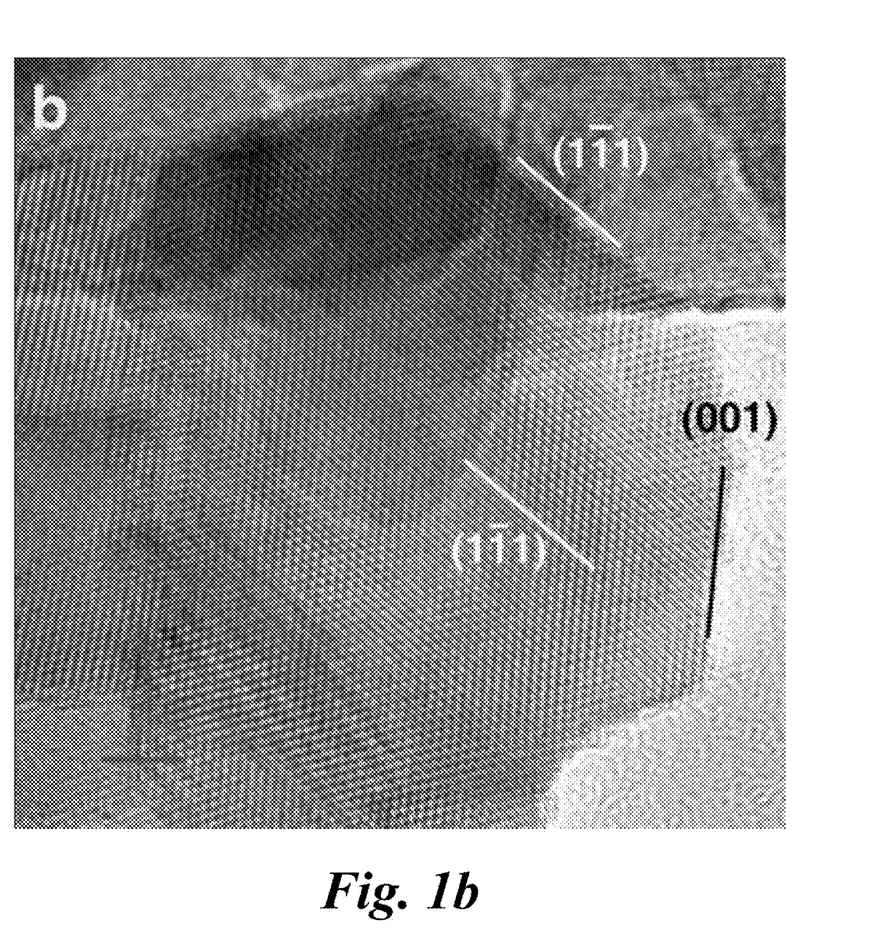

The crystal facets exposed on the nanorod and nanoparticle surfaces were characterized with high resolution TEM, see FIGS. 1a and 1b. The d-spacing (2.83±0.03 Å) measured by HRTEM on the $Co_3O_4$ nanorods was consistent with that of the (220) peaks shown in the X-ray diffraction (XRD) patterns, and according to literature results in the exposure of the {110} family of facets at their surface. In contrast, the Co nanoparticles exhibit {001} and {111} facets at their surfaces, based on the HRTEM image in FIG. 1b, which is also consistent with literature. The difference in the crystallographic facets corresponds to distinct atomic structures being present at the surfaces of nanorods and nanoparticles. Based on literature accounts and HRTEM images, this indicated that the nanoparticles exhibit primarily $Co^{2+}$, while the nanorods have a mixture of $Co^{3+}$ and $Co^{2+}$ on their surfaces, see FIG. 3b. The presence of the different oxidation states of Co on the surface results in substantial differences in the reduction temperature of the respective materials. Temperature programmed reduction (TPR) experiments demonstrate that the $Co^{3+}$ bearing nanorods can be reduced to $Co^0$ at temperature of 533 K, which is approximately 60 K lower than the reduction temperature for the $Co^{2+}$ bearing nanoparticles (593 K). The lower reduction temperature of $Co^{3+}$ is commensurate with the typical reaction conditions for FTS (473-573 K). This suggests a facile ability to reverse oxidation of the catalyst in operando.

Figure 2A:
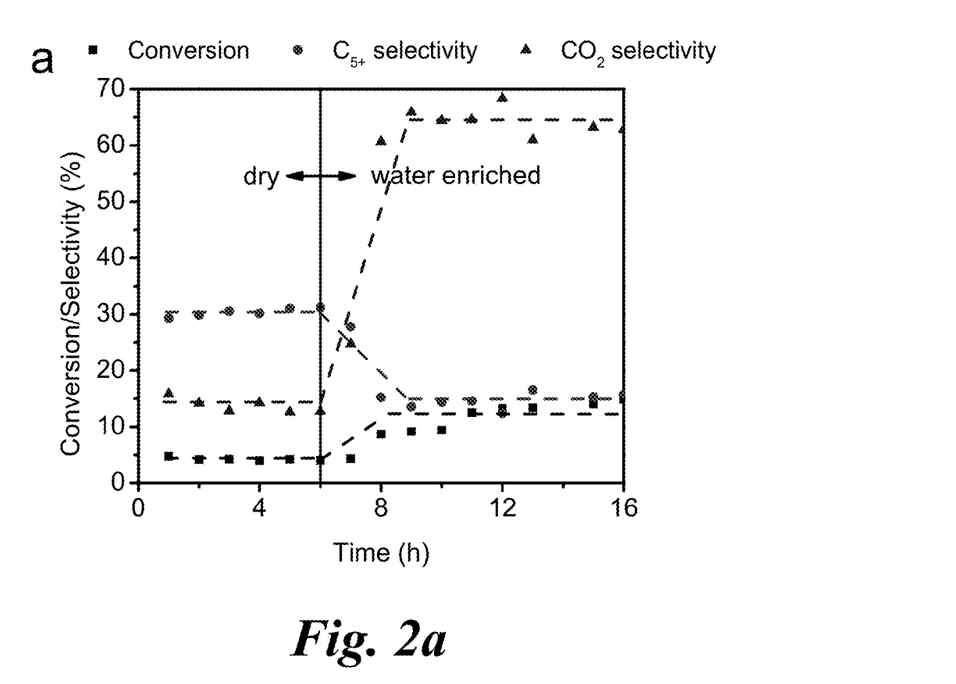
FIGS. 2a and 2b show Fischer-Tropsch synthesis (FTS) on nanoparticles and nanorods, respectively, at different reaction conditions to minimize mass and heat transfer limitations (conversion of CO <15%). At 6 hours, 25 vol. % of water were added to the feed stream. The lines were added as a guide to the eye.

After reduction at 773 K under hydrogen, the $Co_3O_4$ nanoparticles and nanorods were reduced to metallic Co, as indicated by in situ Raman TPR measurements. Subsequently, their FTS activity and selectivity were measured before and during the addition of water (25 vol. %) to the reactant feed. CO conversion rates were kept below 15% to minimize mass and heat transfer limitations, achieved by tuning the reaction temperature for the nanorods to 433 K and for the nanoparticles to 543 K. On the nanoparticles, once the reaction environment was switched to water-rich conditions, the activity and selectivity changed substantially. For instance, the conversion of CO increased from 5%±1% to 13%±3%, the selectivity towards $CO_2$ increased dramatically from about 14%±2% to 65%±4%, and the selectivity towards hydrocarbons with chain length longer than 5 ($C_{5+}$) decreased from 31%±2% to 15%±2%, see FIG. 2a. The effects of water addition observed here are similar to those reported by literature. The changes in $CO_2$ and $C_{5+}$ selectivity and the CO conversion rate can be attributed to the oxidation of surface $Co^0$, which decreases the activity toward long-chain hydrocarbons, but promotes the water-gas-shift reaction to produce $CO_2$.

Figure 2B:
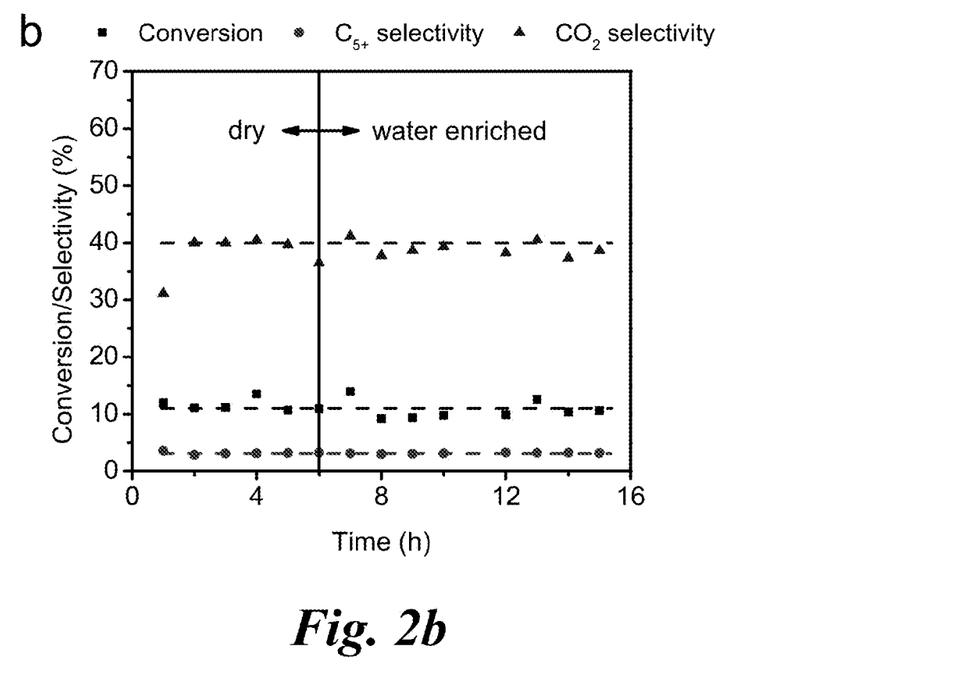
Figure 2C:
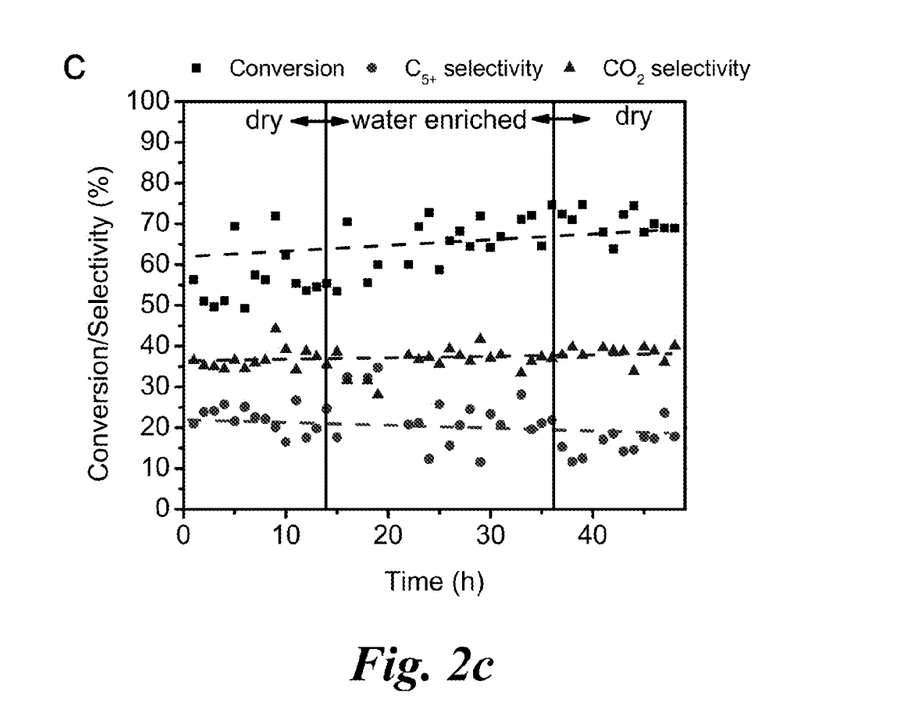

In contrast, the nanorods show no significant change of the selectivity toward $CO_2$ and $C_{5+}$. CO conversion also remained stable at 12%±3%, even after more than 10 hours of exposure to the water rich reaction conditions, as can be seen in FIG. 2b. It should be pointed out that the nanorods were tested at a reaction temperature of 90 K below their TPR measured reduction temperature, and still did not exhibit any changes to their catalytic activity during water-enriched FTS. When the nanorods and nanoparticles were tested under identical feed and temperature conditions, the nanorods exhibited CO conversion rates in excess of 60%, as compared to 6%±1% for the nanoparticles, see FIG. 2c. Here again, no significant change of selectivity towards $CO_2$, $C_{5+}$ was observed for the nanorods, even after 20 hours of exposure to water rich conditions. Under both reaction conditions the catalytic properties of the nanorods were unaffected by the addition of water to the feed throughout the duration of the experiments, while the nanoparticles show strong degradation of their FTS performances after less than an hour of exposure to an oxidative environment. This is a clear indication that, unlike the Co nanoparticles, Co nanorods are very resistant to water oxidation.

Figure 5A:
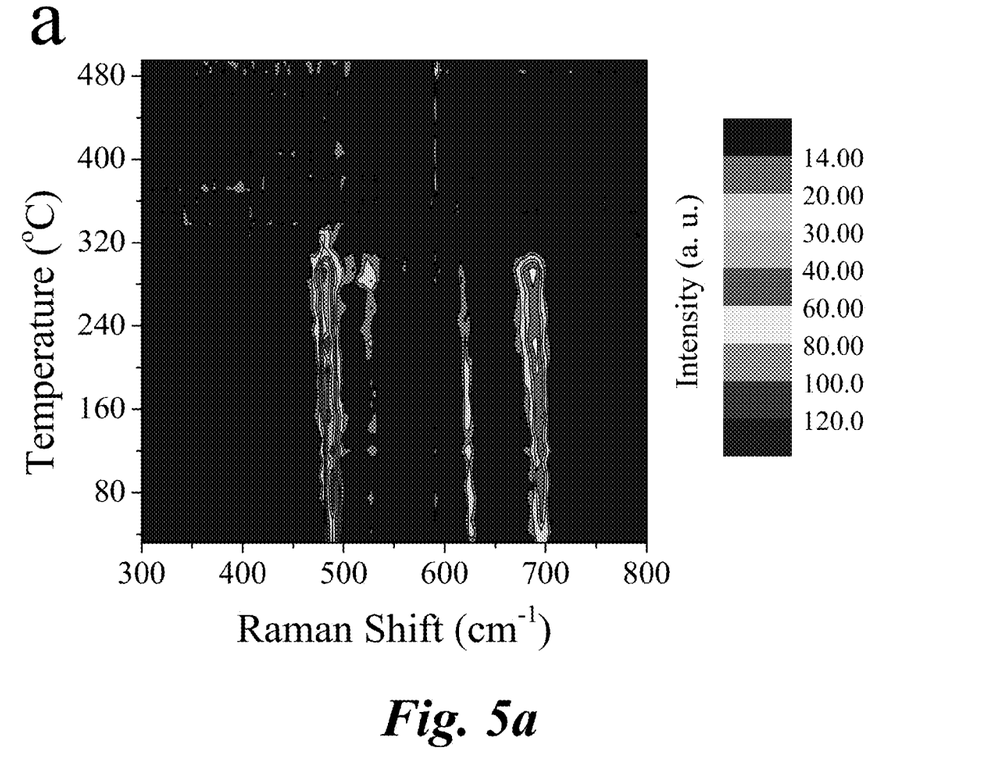
FIGS. 5a and 5b show in situ Raman spectra of nanoparticles and nanorods, respectively, during hydrogen temperature programmed reduction.
Figure 5B:
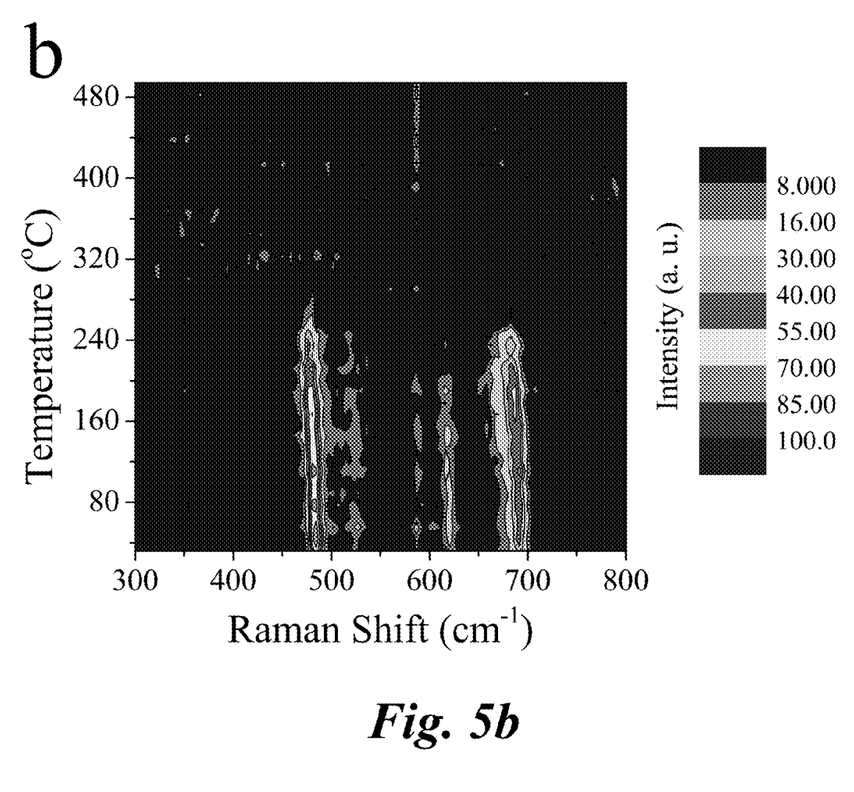

To elucidate the mechanism of the observed resistance to oxidation, in situ Raman spectra were taken on both nanorods and nanoparticles. Prior to catalyst activation by hydrogen reduction, both nanorods and nanoparticles show four Raman peaks located at 482 $cm^{-1}$, 520 $cm^{-1}$, 618 $cm^{-1}$, and 691 $cm^{-1}$, which correspond to the four phonon modes of $Co_3O_4$ ($E_g$, $F_{2g}$, $F_{2g}$, and $A_{1g}$), as shown in FIGS. 5a and 5b. During in situ hydrogen reduction, the oxide peaks disappear at 593 K on the nanoparticles, as compared to 533 K on the nanorods, corresponding to the reduction of the $Co_3O_4$ to Co metal. The difference in reduction temperature coincides well with results from TPR and is another confirmation of the readily reducible nature of the nanorods.

Figure 3A:
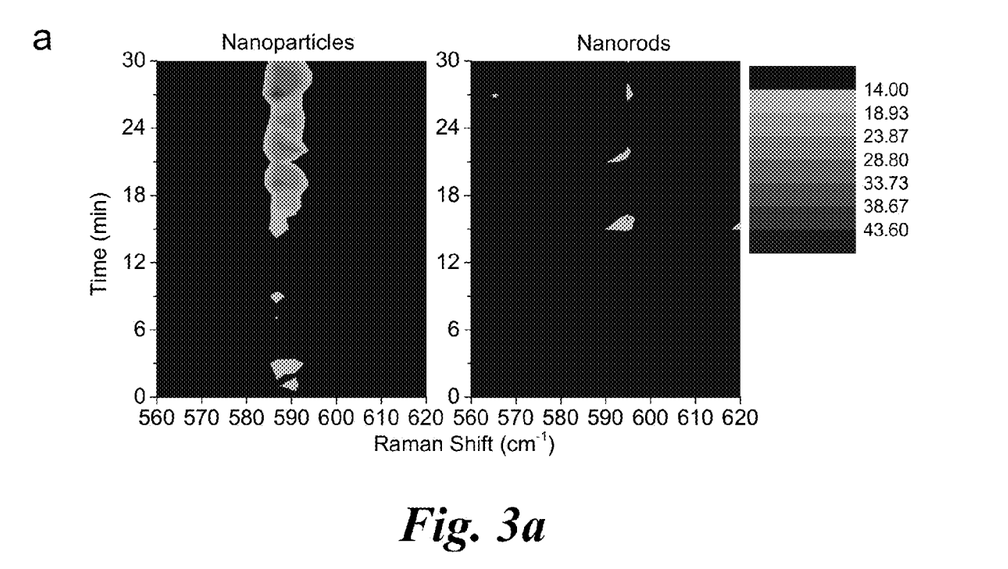
FIG. 3a shows in situ Raman spectra of nanoparticles and nanorods during Fischer-Tropsch reactions. The dash lines represent the start time of water enriched condition during in situ Raman.
Figure 3B:
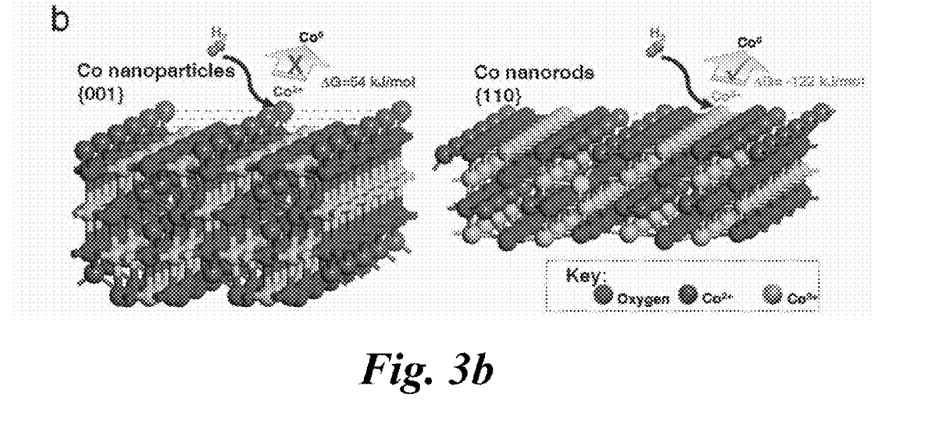
FIG. 3b shows an illustration of the mechanism of recovery for water-oxidized Co nanorods compared to water-oxidized Co nanoparticles.

After reduction at 773 K, in situ Raman spectra were taken to characterize the phase of the catalysts during FTS conditions and water-rich FTS conditions. As shown in FIG. 3a, dosing the nanoparticles with water-rich syngas at 543 K results in the appearance of a peak located at 591 $cm^{-1}$, corresponding to CoOOH, an intermediate for the formation of $Co_3O_4$. The intensity of this peak is correlated to the amount of CoOOH present on the catalyst. This result is consistent with previous experimental observations showing that Co nanoparticles are quickly oxidized by water under FTS reaction conditions, corresponding to the observed change in FTS activity shown in FIG. 2(a). For the Co nanorods, in contrast, in situ Raman shows (FIG. 3a) that the formation of CoOOH is limited and reversible at 543 K. Once the Raman signature for CoOOH is observed, it disappears again within a few minutes due to the reduction of the surface oxide. In conjunction with the FTS reaction data, which clearly shows no change in the activity and selectivity of the Co nanorods during water-rich condition over a period of time exceeding 10 h, the Raman results indicate that the nanorod-based catalyst self-heals during water dosing by reducing the oxide as it is formed.

The mechanism behind the observed differences in the oxidation of the two morphologies can be understood by examining the difference in the reduction potential of the two oxidation states of Co presented at their surfaces. On nanoparticles, only $Co^{2+}$ sites, with a reduction potential to the metallic state of −0.28 V (referring to standard hydrogen electrode set as 0 V), will be preferentially exposed on the outermost surface according to the HRTEM images (FIG. 2b). The reduction potential can be converted to the Gibbs free energy by the Nernst equation ($\Delta G=nEF$; here E, F, $\Delta G$, and n are the reduction potential, the Faraday constant, the Gibbs free energy, and the number of electrons involved in the reaction, respectively). This yields a positive (54 kJ $mol^{-1}$) Gibbs free energy for hydrogen reduction for $Co^{2+}$ to $Co^0$, and indicates that the reaction is unfavorable. Contrarily, on the Co nanorods, $Co^{3+}$ is present on the surface due to the preferential exposing of {110} (shown in FIG. 1a), and the reduction potential to Co metal is 0.42 V, see FIG. 3b. This corresponds to a negative Gibbs free energy (−122 kJ mol-1), marking a favorable reduction of water-oxidized Co. Thus, the reversibility of oxidation on the Co nanorods as observed by in situ Raman spectra, and subsequent insensitivity of activity and selectivity on the nanorods to water dosing, can be attributed to the reduction potential of the $Co^{3+}$ species.

Experimental, Synthesis of $Co_3O_4$ Nanorods and Nanoparticles:

The $Co_3O_4$ nanorods were synthesized according to literature reports. Typically, 4.98 g $Co(OAC)_2.4H_2O$ was added in 60 mL ethylene glycol and magnetic stirred for dissolving. Then the solution was heated up to 160° C. under $N_2$ flow. After the temperature was stabilized, 200 mL 0.2 mol $L^{-1}$ $Na_2CO_3$ aqueous solution was pumped into the solution at the speed of 1.11 mL $min^{-1}$. After dosing of $Na_2CO_3$ solution, the mixture was heated at 160° C. for one more hour. Then, the product was collected by filtering and washing with ethanol. Then, the filtered cake was dried at 50° C. under vacuum overnight. After drying, the product was calcinated at 450° C. for 4 h, which gave the final $Co_3O_4$ nanorods. For the synthesis of $Co_3O_4$ nanoparticles, simply change of the reaction temperature from 160° C. to 80° C. was made, while keeping the other parameters as the same.

Experimental, Fischer-Tropsch Synthesis 0.8 g $Co_3O_4$ nanorods or nanoparticles were reduced at 500° C. under pure hydrogen flow at 100 mL $min^{-1}$ for 5 h before employed as catalyst for Fischer-Tropsch synthesis (FTS). After reduction, the system was cooled down to 270° C. under hydrogen flow, and then gas was switched to syngas (31% CO, 62% $H_2$, and 7% Ar). The GHSV on both nanorods and nanoparticles were kept the same at 2000 mL $h^{-1}$ $g^{-1}$. The reaction temperature for FTS was 270° C., and pressure was maintained at 10 bar with backpressure valve (GO regulator BP3-1A11Q5J111). All the downstream lines after FTS reactors were kept above 160° C. including back pressure valve and injection valve on gas chromatograph (GC). The products from FTS were analyzed on-line with Shimadzu GC 2014 equipped with both thermoconductivity and flame ionization detectors. The GC has two columns, one is packed column (Heysep D) for analyzing CO, $CO_2$, and $C_1$ to $C_6$, and the other one is capillary column (ZB-1 HT) for analyzing all hydrocarbons. The hydrocarbon selectivity was calculated on the carbon basis. After several hours of dry syngas reactions, water was dosed into the system with high performance liquid chromatograph (HPLC) pump (Alltech 426) at rate of 0.01 mL $min^{-1}$ to exam the resistivity of nanorods and nanoparticle to the water oxidation.

Experimental, In situ Raman:

In situ Raman was conducted using laser with wavelength of 632.81 nm. The in situ Raman was started with $H_2$ temperature programmed reduction (TPR), from room temperature to 500° C. at ramping rate of 5° C. $min^{-1}$. After reaching 500° C., the sample was kept reducing at this temperature for 3 more hours. Then the system is cooled down to 270° C., and the gas was switched to syngas (31% CO, 62% $H_2$, and 7% Ar) at 1 bar. After several hours of dry syngas feeding, water was dosed into the system with 25 vol. % in the feed to keep consistent with that during FTS reactions.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A self-healing reaction process, comprising:
exposing a catalyst to a reaction mixture such that hydrocarbons are produced, wherein the reaction mixture comprises carbon monoxide and hydrogen gas, and wherein the catalyst comprises $Co_3O_4$ nanorods that define a {110} facet having both $Co^{2+}$ and $Co^{3+}$ exposed thereon.

2. The self-healing reaction process as in claim 1, wherein the $Co_3O_4$ nanorods have a spinel crystal structure.

3. The self-healing reaction process as in claim 1, wherein the reaction mixture further comprises water.

4. The self-healing reaction process as in claim 3, wherein water serves to oxidize portions of the catalyst, while the exposed $Co^{3+}$ serves to reduce any oxidized portions of the catalyst such that the catalyst is self-healing during reaction conditions.

5. The self-healing reaction process as in claim 1, wherein hydrocarbons have a length of about 5 carbons or more.

6. The self-healing reaction process as in claim 1, wherein the $Co_3O_4$ nanorods have an average diameter of about 10 nm to about 20 nm.

7. The self-healing reaction process as in claim 1, wherein the $Co_3O_4$ nanorods have an average length of about 200 to about 300 nm.

* * * * *